(12) United States Patent
Nagatomi et al.

(10) Patent No.: US 11,001,798 B2
(45) Date of Patent: May 11, 2021

(54) APPARATUS AND METHOD FOR NON-CONTACT ELECTRICAL STIMULATION OF CELLS IN LIQUID CULTURE MEDIUM

(71) Applicants: TOHOKU UNIVERSITY, Miyagi (JP); IFG CORPORATION, Miyagi (JP)

(72) Inventors: Ryoichi Nagatomi, Miyagi (JP); Toshiyuki Takagi, Miyagi (JP); Shinichi Izumi, Miyagi (JP); Toshihiko Abe, Miyagi (JP); Hitoshi Mori, Miyagi (JP); Kenji Yashima, Miyagi (JP); Kazumi Mori, Miyagi (JP)

(73) Assignees: IFG CORPORATION, Miyagi (JP); TOHOKU UNIVERSITY, Miyagi (JP)

( * ) Notice: Subject to any disclaimer, the term of this patent is extended or adjusted under 35 U.S.C. 154(b) by 440 days.

(21) Appl. No.: 16/302,350

(22) PCT Filed: May 19, 2017

(86) PCT No.: PCT/JP2017/018850
§ 371 (c)(1),
(2) Date: Nov. 16, 2018

(87) PCT Pub. No.: WO2017/204111
PCT Pub. Date: Nov. 30, 2017

(65) Prior Publication Data
US 2019/0161722 A1    May 30, 2019

(30) Foreign Application Priority Data

May 26, 2016    (JP) .............................. JP2016-105075

(51) Int. Cl.
*C12M 1/42*    (2006.01)
*C12M 1/00*    (2006.01)
(Continued)

(52) U.S. Cl.
CPC .............. *C12M 35/06* (2013.01); *A61N 2/006* (2013.01); *A61N 2/02* (2013.01); *C12M 23/02* (2013.01); *C12M 23/20* (2013.01); *C12M 35/02* (2013.01)

(58) Field of Classification Search
CPC ...... C12M 35/06; C12M 23/02; C12M 23/20; C12M 35/02; A61N 2/006; A61N 2/02
See application file for complete search history.

(56) References Cited

U.S. PATENT DOCUMENTS

| | | | | |
|---|---|---|---|---|
| 6,040,192 A | * | 3/2000 | Tuunanen | B01L 3/02 436/177 |
| 7,267,800 B2 | * | 9/2007 | Takii | G01N 35/10 422/501 |

(Continued)

FOREIGN PATENT DOCUMENTS

| | | | | |
|---|---|---|---|---|
| DE | 102006015550 A1 | * | 10/2007 | ............ C12M 35/02 |
| JP | 2004-129603 A |   | 4/2004 | |

(Continued)

OTHER PUBLICATIONS

DE102006015550 Machine translation (Year: 2021).*
(Continued)

*Primary Examiner* — William H. Beisner
*Assistant Examiner* — Danielle B Henkel
(74) *Attorney, Agent, or Firm* — Lucas & Mercanti, LLP (57) ABSTRACT

The present invention provides an apparatus for applying electrical stimulation to cells in a liquid culture medium without using electrodes immersed in the liquid culture medium. This apparatus is an electrical stimulation apparatus A for electrically stimulating cells in a liquid culture medium (2). A liquid culture medium vessel (3) includes: a ring-shaped recess (7) for holding the liquid culture medium (2); and a through hole (6) formed within the ring-shaped recess (7). A magnetic core (1) is made of a magnetic (Continued)

material and disposed such that a portion thereof is inserted through the through hole (6) of the liquid culture medium vessel (3). An excitation coil (5) is wound around the magnetic core (1). A coil power supply (8) supplies a varying current to the excitation coil (5).

5 Claims, 8 Drawing Sheets

(51) Int. Cl.
*A61N 2/00* (2006.01)
*A61N 2/02* (2006.01)

(56) References Cited

U.S. PATENT DOCUMENTS

| | | | | |
|---|---|---|---|---|
| 2009/0311733 A1* | 12/2009 | Korpela | ............ | G01N 33/54326 435/29 |
| 2012/0252088 A1* | 10/2012 | Zhang | ............ | C12N 1/02 435/173.9 |
| 2013/0043191 A1* | 2/2013 | Park | ............ | C12M 33/06 210/695 |
| 2016/0032234 A1* | 2/2016 | Rosell Ferrer | ......... | C12M 35/04 435/173.8 |
| 2017/0080430 A1* | 3/2017 | Fu | ............ | B01L 9/06 |
| 2017/0204358 A1* | 7/2017 | Navran, Jr. | ............ | C12M 25/14 |
| 2019/0054442 A1* | 2/2019 | Xu | ............ | B01J 19/12 |

FOREIGN PATENT DOCUMENTS

| | | |
|---|---|---|
| JP | 2004-290180 A | 10/2004 |
| JP | 2005-027501 A | 2/2005 |
| JP | 2014-161323 A | 9/2014 |
| WO | 2008-056414 A1 | 2/2010 |

OTHER PUBLICATIONS

English translation of written opinion from PCTJP17/018850 (Year: 2017).*
International Search Report dated Aug. 15, 2017 from corresponding International Application No. PCT/JP2017/018850 and English translation.
Yumi Kawahara, et al., "Effects of Electrical Stimulation of Myoblasts", Japanese Physical Therapy Association, 2005 (0), 2006, A0617-A0617 and English translation.
Hideaki Fujita, et al., "Accelerated de novo sarcomere assembly by electric pulse stimulation in C2C12 myotubes", Experimental Cell Research, vol. 313, 2007, pp. 1853-1865.
Sumihiro Koyama, et al., "Mechanisms of Electrically Regulated Cellular Functions", Chemistry and Biology, vol. 38, No. 8, 2000, pp. 503-507 and English translation.

* cited by examiner

APPARATUS AND METHOD FOR NON-CONTACT ELECTRICAL STIMULATION OF CELLS IN LIQUID CULTURE MEDIUM

This Application is a 371 of PCT/JP2017/018850 filed May 19, 2017, which, in turn, claimed the priority of Japanese Patent Application No. 2016-105075 filed on May 26, 2016, and both applications are incorporated herein by reference.

TECHNICAL FIELD

The present invention relates to an apparatus for electrically stimulating cells in a liquid culture medium in a non-contact manner without immersing electrodes in the liquid culture medium, and a method for electrical stimulation using the apparatus.

BACKGROUND ART

It has been recently found that it is possible to control various cellular functions by electrically stimulating cells in a liquid culture medium. The effects that have been reported so far include: (1) expression of specific genes and production of proteins; (2) induction of cell differentiation; (3) change in cell morphology; (4) effect of reducing membrane fluidity; and (5) effect of delaying cell growth.

As an example of the effect (1) "expression of specific genes and production of proteins", it has been confirmed that a protein (Cx43) that promotes differentiation of muscle cells is expressed by applying intermittent voltage changes to a liquid culture medium in the process of culturing myoblasts (Non-Patent Literature 1).

It has also been confirmed that myoblasts can acquire contractile ability after being cultured under electrical stimulation in a particular direction (Non-Patent Literature 2).

An example of the effect (2) "induction of cell differentiation" by electrical stimulation is induction of differentiation of pheochromocytoma (PC12) cells of rats' adrenal medulla. When these PC12 cells are cultured in the presence of nerve growth factor (NGF), they differentiate into neuron-like cells and their neurites grow toward the distribution of NGF. A recent study has found that PC12 cells differentiate into neuron-like cells when they are cultured for 96 hours under application of a voltage that varies in a rectangular waveform, even in the absence of NGF (see Non-Patent Literature 3).

Patent applications have also been filed for electrical stimulation-induced cell culture methods as described above. Patent Literatures 1 and 2 each disclose a cell differentiation inducing method in which cells are electrically stimulated for a predetermined time or more using electrodes so as to induce differentiation of the cells.

On the other hand, a patent application has also been filed for a technique for controlling cellular functions using a magnetic field instead of electrical stimulation. Patent Literature 3 discloses an apparatus for applying a high-frequency alternating magnetic field to cells to increase the intracellular concentration of calcium ions so as to promote the synthesis and extracellular release of neurotrophic factors.

CITATION LIST

Non-Patent Literature

[NPTL 1] Yumi KAWAHARA, Chika UMEDA, Reiko YOSHIMOTO, Akira SASAKI, Shuliang WU, and Rui, YUGE, "Kingasaibo eno Denki Shigeki Koka (Effects of Electrical Stimulation of Myoblasts)", Japanese Physical Therapy Association, 2005 (0), 2006, A0617-A0617

[NPTL 2] Hideaki FUJITA, Taku NEDACHI, Makoto KANZAKI, "Accelerated de novo sarcomere assembly by electric pulse stimulation in C2C12 myotubes", Experimental Cell Research. Vol. 313, 2007, pp. 1853-1865

[NPTL 3] Sumihiro KOYAMA, Masuo AIZAWA "Denki Shigeki niyoru Saibo Kino no Seigyo (Mechanisms of Electrically Regulated Cellular Functions)", Kagaku to Seibutsu (Chemistry and Biology), Vol. 38. No. 8, 2000, pp. 503-507

Patent Literature

[PTL 1] Japanese Laid-Open Patent Publication No. 2004-129603

[PTL 2] Japanese Laid-Open Patent Publication No. 2005-027501

[PTL 3] Domestic Re-Publication of PCT International Publication No. 2008-056414

SUMMARY OF INVENTION

Technical Problem

The methods for controlling cells using electrical stimulation as shown above are expected to be applied in various medical fields in the future but have some problems. A particularly important problem is the problem of electrodes. In order to apply electrical stimulation to a liquid culture medium, electrodes must be brought into contact with (immersed into) the liquid culture medium before a voltage is applied thereto.

When a voltage is applied, electrons are transferred between the liquid culture medium and the electrodes, and as a result, electrode metals are ionized and the resulting ions are released into the liquid culture medium. Then, the ions in the liquid culture medium receive electrons and deposit on the electrodes.

Water ($H_2O$) as the main component of the liquid culture medium is split into hydrogen and oxygen by electrolysis, which are released into the liquid culture medium. As a result, the pH of the liquid culture medium changes, and in addition, the concentration of ions of a specific element also changes, which make it difficult to keep the culture environment stable. Therefore, it is necessary to adjust the chemical environment of the liquid culture medium on a regular basis, which is a problem. The change in the chemical environment of the liquid culture medium means the lack of stable cell culture conditions, which is the problem that could affect the reliability of studies concerned.

In the process of cell culture for clinical applications, it is extremely important to maintain aseptic conditions. Since a cell culture incubator itself is delivered in a sterile condition, it is not necessary to spend time and effort to sterilize the cell culture incubator unless the incubator is used again. In contrast, all electrodes are used again as a rule. Therefore, it is necessary to sterilize the electrodes for each experiment, which makes it difficult to maintain aseptic conditions. If an apparatus capable of delivering electrical stimulation without the need for sterilization is available, the workload of medical researchers would be significantly reduced.

The present invention has been made in view of the above problems, and it is a primary object of the present invention to provide an apparatus for electrically stimulating cells in a liquid culture medium without using electrodes immersed in the liquid culture medium and a method for such non-contact electrical stimulation using this apparatus. It is a secondary object of the present invention to provide such an apparatus and method in which the current density flowing in the liquid culture medium can be changed locally so as to apply various levels of electrical stimulation to the cells in the liquid culture medium or to apply low-level electrical stimulation to only a fraction of the cells.

Solution to Problem

In order to achieve the above objects, the present invention has solved the above problems using the following techniques. The invention as set forth in claim 1 (FIG. 1) is an electrical stimulation apparatus A for electrically stimulating cells in a liquid culture medium 2, including:
a liquid culture medium vessel 3 including: a ring-shaped recess 7 for holding a liquid culture medium 2; and a through hole 6 formed within the ring-shaped recess 7;
a magnetic core 1 made of a ferromagnetic material and disposed such that a portion of the magnetic core 1 is inserted through the through hole 6 of the liquid culture medium vessel 3;
an excitation coil 5 wound around the magnetic core 1; and
a coil power supply 8 for supplying a varying current to the excitation coil 5.

According to the invention of claim 1, when the excitation coil 5 is energized with a varying current, a varying magnetic flux is generated in the magnetic core 1, and the varying magnetic flux induces a varying eddy current U (and a varying electric field) in the liquid culture medium 2 held in the liquid culture medium vessel 3. The cells in the liquid culture medium vessel 3 can be electrically stimulated by the induced eddy current U (and electric field), in other words, without using electrodes immersed in the liquid culture medium and thus without contact with the liquid culture medium 2.

The invention as set forth in claim 2 is the electrical stimulation apparatus A, wherein the magnetic core 1 forms a closed magnetic path.

According to the invention of claim 2, the demagnetizing field in the magnetic core 1 is reduced to near-zero. Thus, it is possible to generate a magnetic flux efficiently in the magnetic core 1.

The invention as set forth in claim 3 is the electrical stimulation apparatus A, wherein the ring-shaped recess 7 of the liquid culture medium vessel 3 includes a reduced path 7a serving as a current-carrying path for an eddy current U induced in the liquid culture medium 2, and the reduced path 7a has a current-carrying cross-sectional area S1 that is smaller than a current-carrying cross-sectional area S2 of a portion other than the reduced path 7a of the ring-shaped recess 7.

According to the invention of claim 3, it is possible to obtain, in the reduced path 7a of the ring-shaped recess 7, a current density (and an electric field) that is (are) higher than in the portion other than the reduced path 7a. Therefore, the reduced path 7a is useful for selective stimulation of only a portion of the cells in the liquid culture medium 2 (i.e., cells present in the reduced path 7a) or low-level electrical stimulation of only a fraction of the cells instilled into the reduced path 7a.

The invention as set forth in claim 4 is the electrical stimulation apparatus A, wherein the magnetic core 1 is composed of electromagnetic steel sheets 9 laminated in a direction perpendicular to a direction g of a magnetic flux generated in the magnetic core 1 (in other words, electromagnetic steel sheets 9 laminated in a direction in which the lamination plane is parallel to the magnetic flux direction g).

According to the invention of claim 4, it is possible to minimize the eddy current loss in the magnetic core 1. Thus, it is possible not only to prevent heat generation from the magnetic core 1 but also to reduce the energy required for the apparatus.

The invention as set forth in claim 5 is a method for electrical stimulation of target cells using the electrical stimulation apparatus A according to claim 1, including:
introducing a liquid culture medium 2 containing target cells into the ring-shaped recess 7 formed in the liquid culture medium vessel 3;
disposing the magnetic core 1 made of a ferromagnetic material such that a portion of the magnetic core 1 is inserted through the through hole 6 formed within the ring-shaped recess 7 of the liquid culture medium vessel 3; and
energizing the excitation coil 5 wound around the magnetic core 1 to generate a magnetic flux in the magnetic core 1, so that the magnetic flux induces a varying eddy current U (and a varying electric field) in the liquid culture medium 2 held in the liquid culture medium vessel 3 and thereby the target cells contained in the liquid culture medium 2 in the ring-shaped recess 7 are electrically stimulated by the induced eddy current U (and electric field).

Advantageous Effects of the Invention

As described above, the use of the electrical stimulation apparatus of the present invention makes it possible to electrically stimulating cells in a liquid culture medium without using electrodes immersed in the liquid culture medium and thus without contact with the liquid culture medium. Thereby, it is possible not only to maintain the chemical environment in the liquid culture medium stable and reduce the frequency of maintenance for controlling the liquid culture medium but also to narrow the cause of change in the components of the liquid culture medium down to the change in the biological activities of the cells. Thus, more reliable studies can be done. In addition, since electrodes immersed in the liquid culture medium are not used, there is no need for sterilization, which makes it possible to provide an unprecedentedly clean and easy-to-use electrical stimulation apparatus for studies of current medical practice.

DESCRIPTION OF EMBODIMENTS

The present inventors have conducted intensive studies for the purpose of generating a varying eddy current U (and a varying electric field) in a liquid culture medium 2 (in other words, using a varying magnetic field to apply an electric field to the liquid culture medium 2 and thereby generating an induced current, i.e., the "varying eddy current U", in the liquid culture medium 2) without using electrodes immersed in the liquid culture medium, which are essential for conventional apparatuses.

As a result, the following effects can be obtained. First, since a magnetic core 1 is used to cause a focused and rapidly changing magnetic flux to pass through the through hole 6 of the ring-shaped liquid culture medium vessel 3, it is possible to induce an eddy current U and others sufficient for stimulating the cells in the liquid culture medium 2.

Second, since a portion of the current-carrying path in the liquid culture medium 2 (i.e., the reduced path 7a) having a current-carrying cross-sectional area S1 that is smaller than a current-carrying cross-sectional area S2 of the other portion of the current-carrying path is provided, it is possible to locally increase the current density in the reduced path 7a and to apply stronger electrical stimulation to the cells present in that portion 7a.

Third, since the magnetic core 1 having a closed magnetic path structure is used, it is possible to induce the eddy current U more efficiently.

Fourth, since laminated silicon steel (or ferrite, laminated permalloy, or laminated amorphous) sheets are used as the material of the magnetic core 1, it is possible to minimize the influence of the eddy current U and thus to generate a strong induced electric field.

Figure 1:
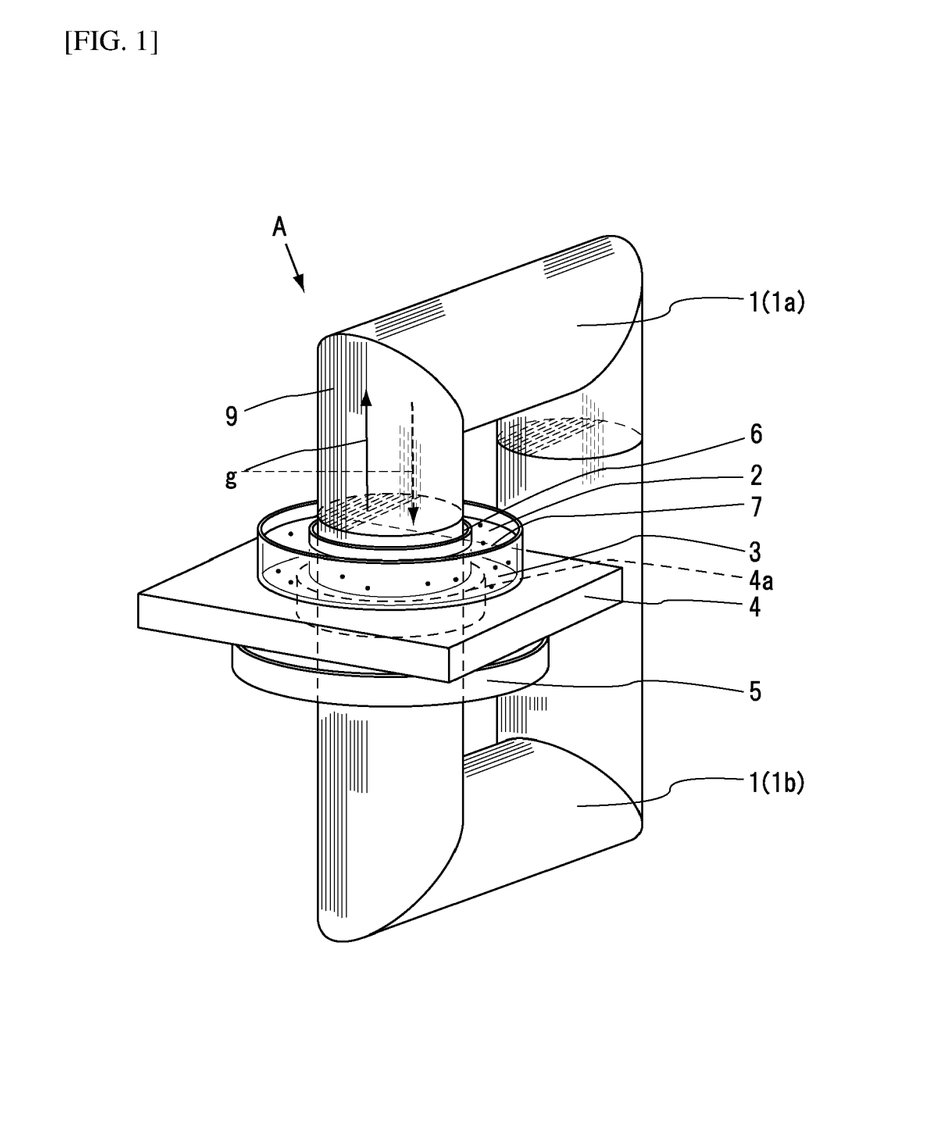
FIG. 1 is a perspective view of a first embodiment of the present invention in an energized state.

Hereinafter, the present invention will be described with reference to the diagrams. As shown in FIG. 1, the apparatus A is mainly composed of a liquid culture medium vessel 3, a magnetic core 1, an excitation coil 5, and a coil power supply 8 for supplying a varying current (a pulsed or alternating current) to the excitation coil 5.

The liquid culture medium vessel 3 is a container having a circular ring-shaped or polygonal (such as rectangular) ring-shaped plan view. A circular or polygonal (such as rectangular) through hole 6 is formed at the center of the liquid culture medium vessel 3, and an open top recess 7 having a circular ring-shaped or polygonal (such as rectangular) ring-shaped plan view is formed around the through hole 6 so as to hold the liquid culture medium 2 therein.

Figure 6:
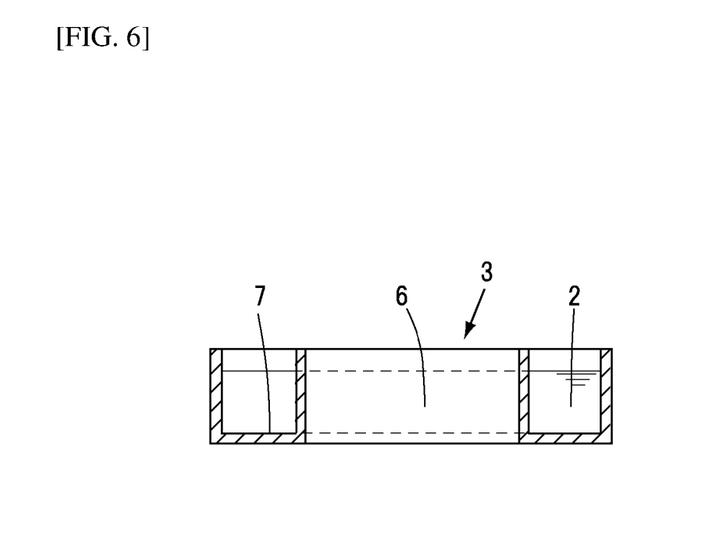
FIG. 6 is a front cross-sectional view of FIG. 5.

In the liquid culture medium vessel 3 shown in FIG. 6, the ring-shaped recess 7 has, along its entire circumference, a constant current-carrying cross-sectional area S2 in the longitudinal cross section passing through the center of the through hole 6 in FIG. 6 (that is, the liquid culture medium 2 has a constant longitudinal cross-sectional area).

Figure 7:
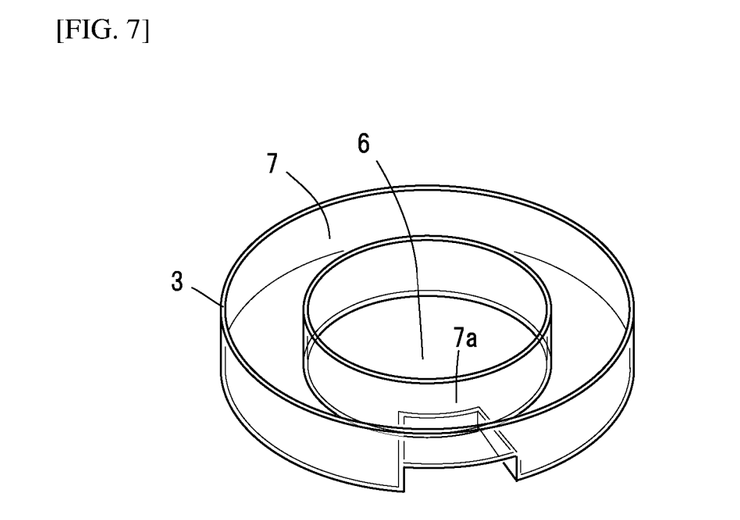
FIG. 7 is a perspective view of a second example of the liquid culture medium vessel used in the present invention.
Figure 8:
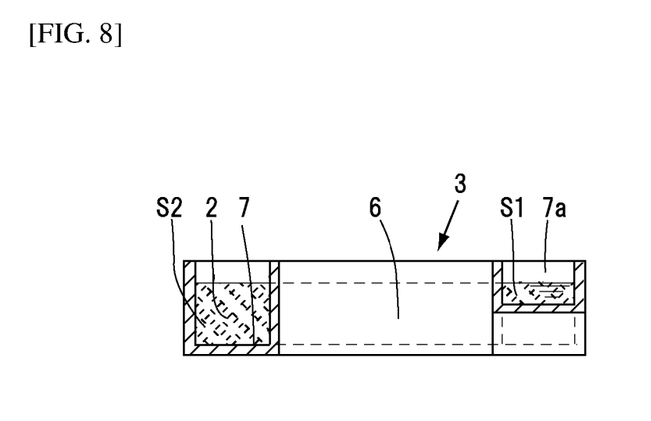
FIG. 8 is a front cross-sectional view of FIG. 7.
Figure 9:
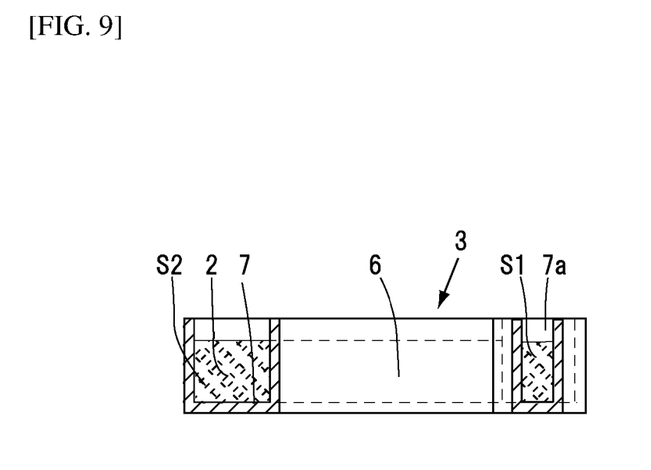
FIG. 9 is a front cross-sectional view of another example of FIG. 7.

In contrast, FIG. 7 to FIG. 9 show modified examples of the liquid culture medium vessel 3 shown in FIG. 6, and these examples each have a reduced path 7a formed in a portion of the ring-shaped recess 7. In the longitudinal cross section passing through the center of the through hole 6, the reduced path 7a has a current-carrying cross-sectional area S1 that is smaller than the current-carrying cross-sectional area S2 of the other portion of the ring-shaped recess 7. It should be noted that FIG. 8 shows an example of the reduced path 7a having a depth shallower than the depth of the other portion and FIG. 9 shows another example of the reduced path 7a having a groove width narrower than the width of the other portion in plan view.

When electrical stimulation is applied, an eddy current U is formed in the ring-shaped recess 7 as a current-carrying path. The through hole 6 is formed within the ring-shaped recess 7 of the liquid culture medium vessel 3 as described above, and a portion of the magnetic core 1 made of a ferromagnetic material is inserted through the through hole 6. A conductor serving as the excitation coil 5 is wound around the magnetic core 1, and a coil power supply 8 for supplying a varying current to the excitation coil 5 is connected thereto by cables (not shown).

The magnetic core 1 is composed of ferromagnetic sheets such as laminated silicon steel sheets as described above. When the magnetic core 1 is composed of laminated silicon steel sheets as electromagnetic steel sheets 9 (or any other laminated ferromagnetic sheets), the sheets are laminated in a direction perpendicular to the magnetic flux direction g of the magnetic core 1 (in other words, in a direction in which the lamination plane is parallel to the magnetic flux direction g).

The magnetic core 1 may have any shape as long as a portion thereof can be inserted through the through hole 6 of the liquid culture medium vessel 3. Examples of the shape include a rod shape, a U shape (or a horseshoe shape), and a hollow rectangular shape forming a closed magnetic path (FIGS. 1 to 4 and 10). The magnetic core 1 having a hollow rectangular shape can be separated into upper and lower two parts, i.e., a U-shaped upper core 1a and a U-shaped lower core 1b, because the magnetic core 1 must be disposed such that a portion thereof is inserted through the through hole 6, as described above.

Figure 2:
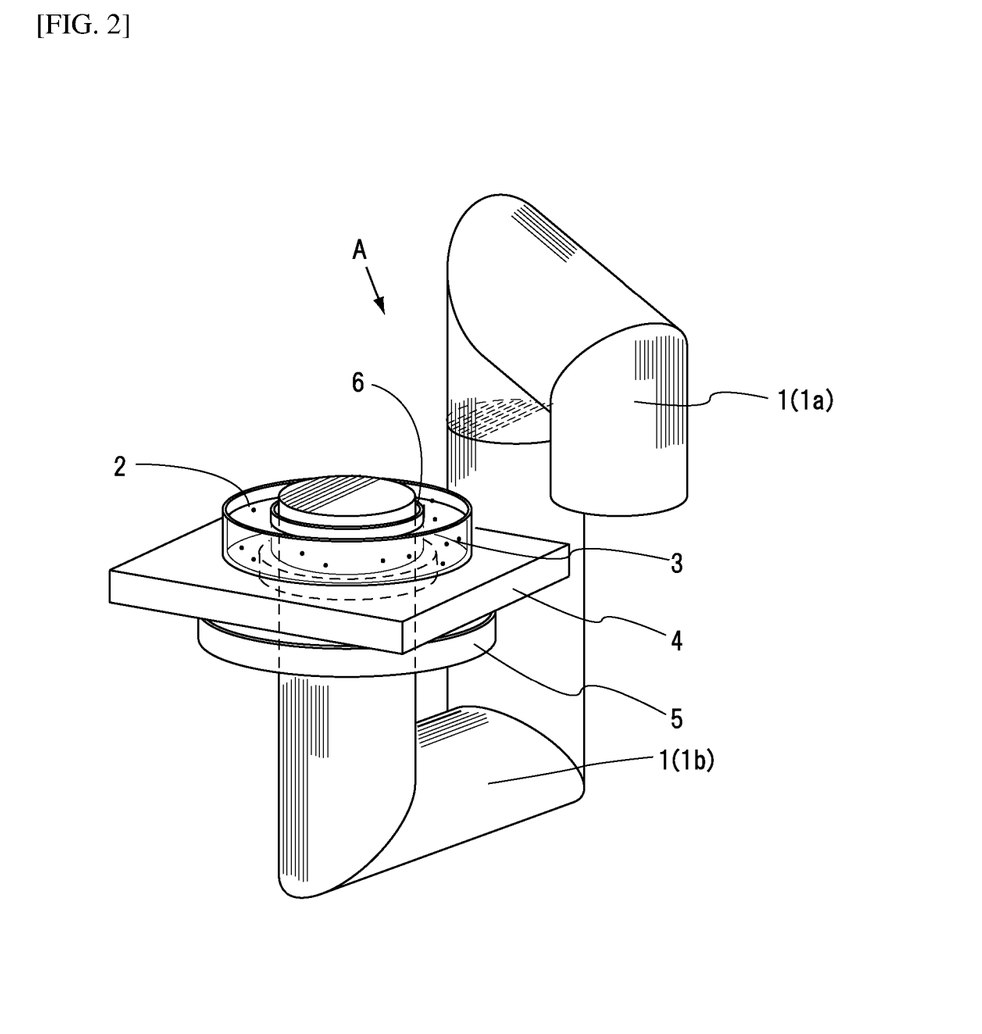
FIG. 2 is a perspective view of FIG. 1 when a liquid culture medium vessel is placed or replaced.
Figure 3:
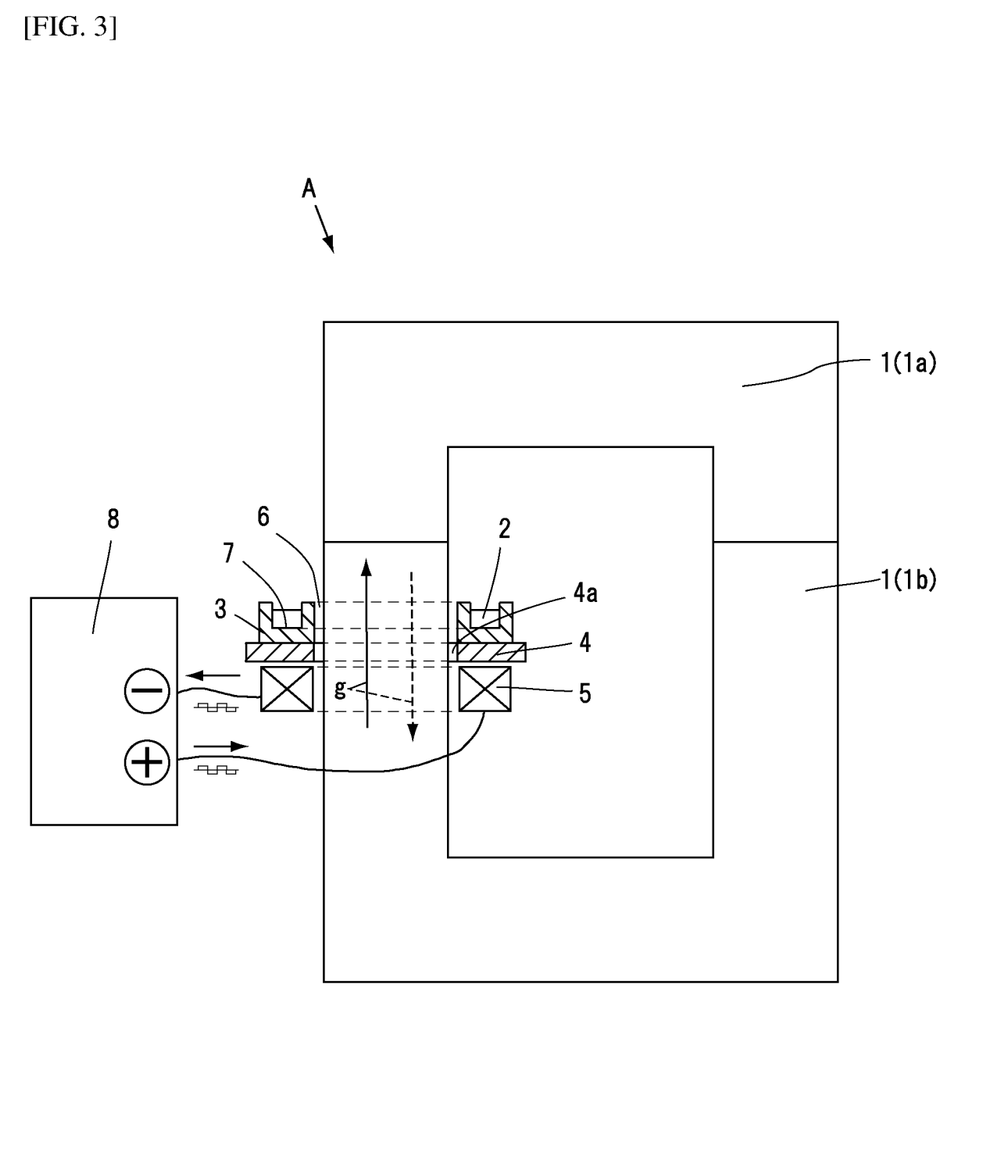
FIG. 3 is a front cross-sectional view of FIG. 1.
Figure 10:
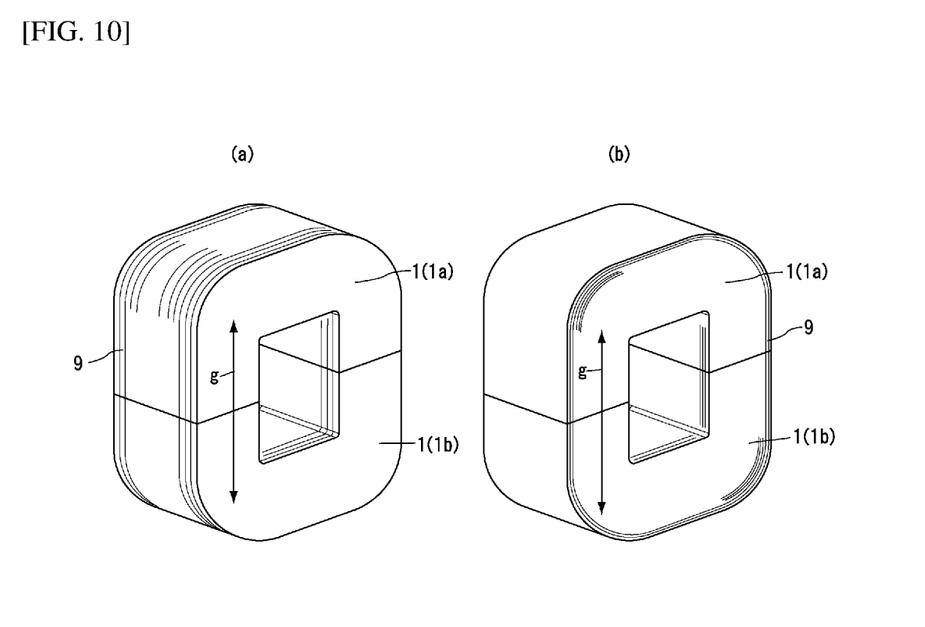
FIG. 10 shows perspective views of examples (a) and (b) of a magnetic core of the present invention.

The transverse cross-sectional shape of the magnetic core 1 is, for example, a circular shape as shown in FIGS. 1 and 2, a rectangular shape (more specifically, a polygonal shape including a rectangular shape) as shown in FIG. 10.

The magnetic core 1 having a circular transverse cross section is obtained by stacking electromagnetic steel sheets 9 (or any other laminated ferromagnetic sheets as described above) having gradually decreasing widths one after another on both surfaces of a widest electromagnetic steel sheet 9 so as to form a circular transverse cross section. The magnetic core 1 having a rectangular transverse cross section is obtained by stacking U-shaped and reverse U-shaped electromagnetic steel sheets 9 respectively so as to form a rectangular transverse cross section ((a) in FIG. 10), or by winding an electromagnetic steel strip around a rectangular mandrel many times and cut the resulting core in half ((b) in FIG. 10).

Next, the principle of operation of the present invention will be described. When a rapidly changing excitation current (i.e., a varying current such as a pulsed excitation current or an alternating excitation current) is supplied from the coil power supply 8 to the excitation coil 5 through the cables, the magnetic core 1 is excited by a magnetomotive force generated by the excitation coil 5, and a varying magnetic flux is generated in the magnetic core 1.

Since the magnetic core 1 is made of a ferromagnetic material, its magnetic flux density is considerably high. For example, when the magnetic core 1 having a closed magnetic path (FIG. 1) is formed using silicon steel sheets, it can produce a magnetic flux density of up to about 2.0 Tesla (T).

When the magnetic core 1 is formed using an iron-based amorphous material, it can produce a magnetic flux density of about 1.5 T.

The magnetic flux in the magnetic core rapidly changes in synchronization with a rapid change in the excitation current. Since the magnetic core 1 is disposed such that a portion thereof is inserted through the through hole 6 of the liquid culture medium vessel 3, this high-density varying magnetic flux passes through the ring-shaped recess 7 of the liquid culture medium vessel 3. As a result, an electric field and an eddy current U are created in the liquid culture medium 2 by electromagnetic induction to cancel this varying magnetic flux. Thus, cells in the liquid culture medium 2 are stimulated.

Figure 12:
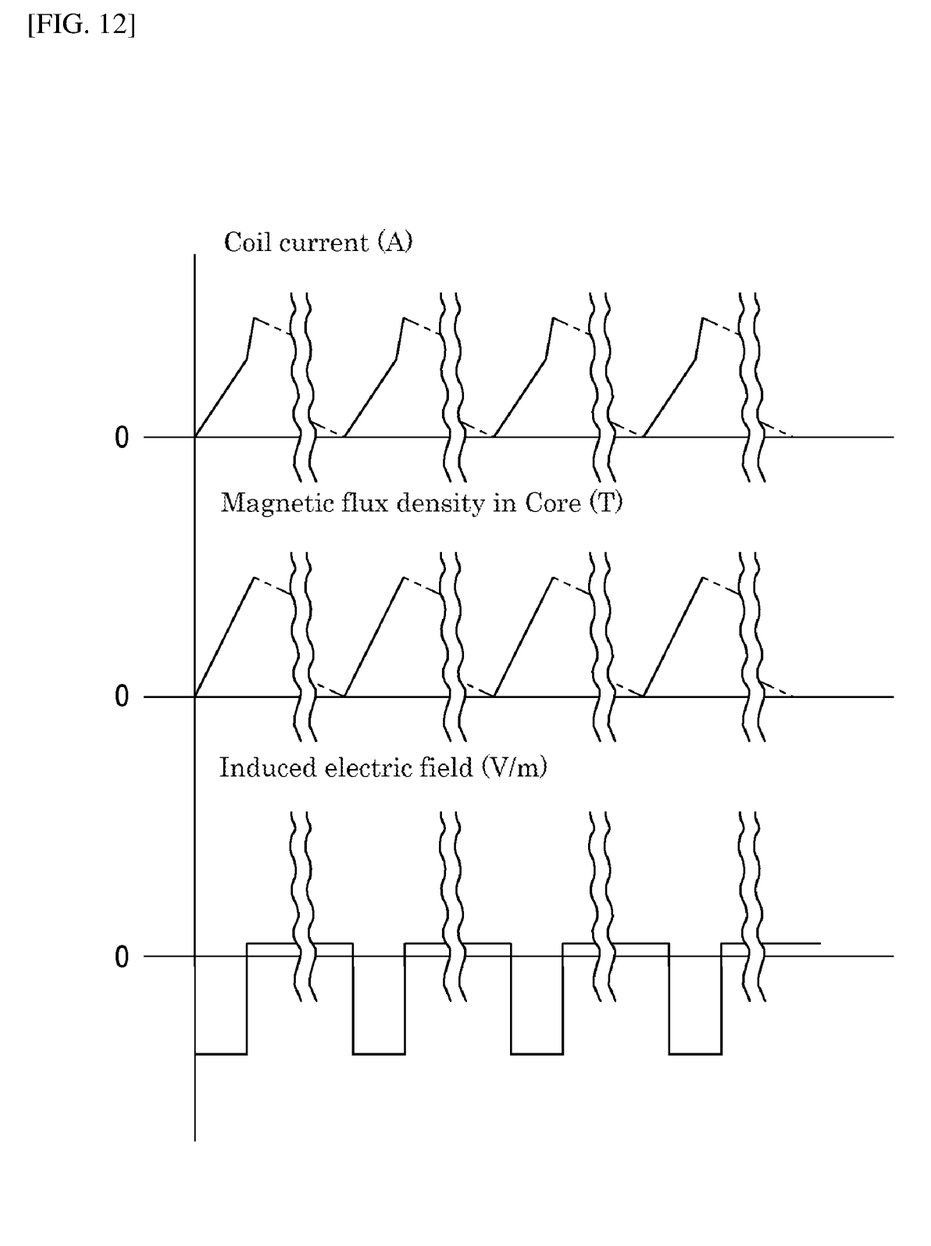
FIG. 12 illustrates a time-series graph showing the relationship among the coil current, the magnetic flux density in a core, and the induced electric magnetic field in the present invention.

FIG. 12 shows an example of the waveform of the current flowing in the excitation coil 5, the waveform of the magnetic flux density in the core, and the induced electric field induced in the liquid culture medium 2 when induced electric field pulses are generated. The magnitude of the induced electric field is proportional to the rate of change in the magnetic flux. Therefore, in order to maintain the induced electric field constant, it is desirable that the change of the magnetic flux in the magnetic core 1 is maintained at a constant rate. In order to cause the magnetic flux to change periodically, it is necessary to increase the change in the current as the magnetic flux density in the magnetic core 1 increases to saturation.

Figure 5:
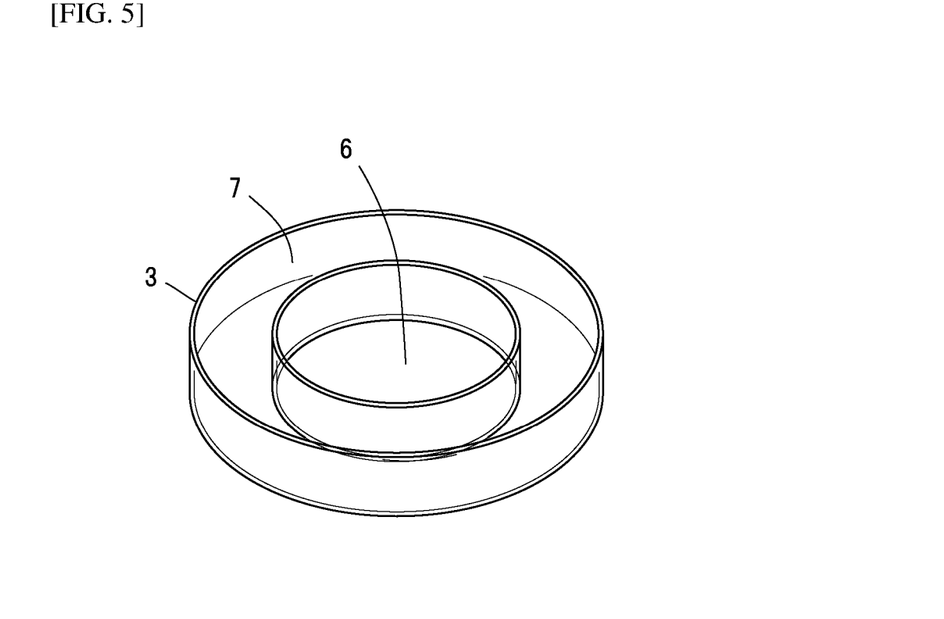
FIG. 5 is a perspective view of a first example of a liquid culture medium vessel used in the present invention.
Figure 11:
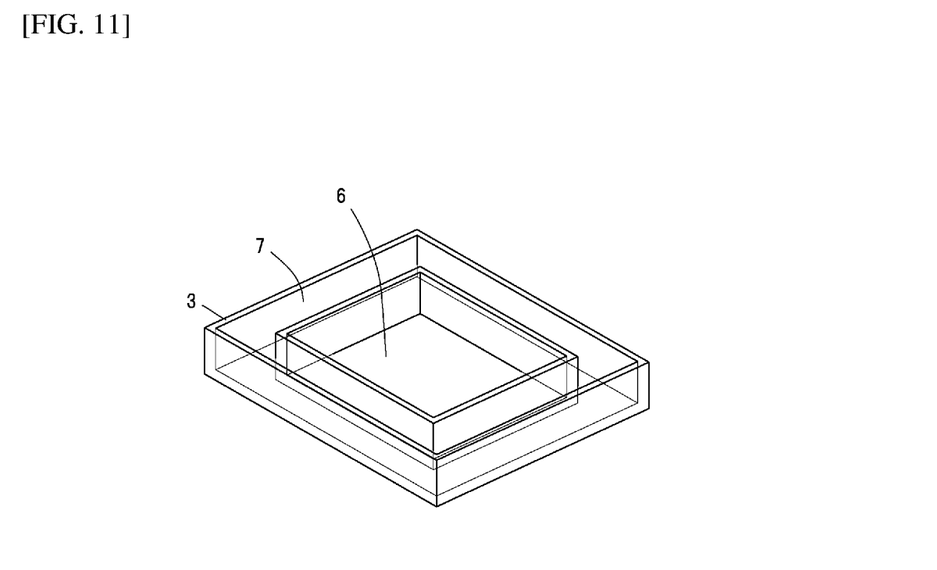
FIG. 11 is a perspective view of a third example of the liquid culture medium vessel used in the present invention.

FIG. 5 to FIG. 9 and FIG. 11 show examples of the above-described liquid culture medium vessel 3. A circular vessel 3 shown in FIG. 5 is characterized in that an almost uniform electric field can be generated over the entire circumference thereof. On the other hand, a rectangular vessel 3 shown in FIG. 11 is characterized in that the electric field density and the eddy current density generated at the four corners are different from those generated along the four sides thereof. In order to prevent the eddy current U from flowing in the liquid culture medium vessel 3 when electrical stimulation is applied, the liquid culture medium vessel 3 must be made of a non-magnetic and non-electrically conductive material such as glass.

Figure 4:
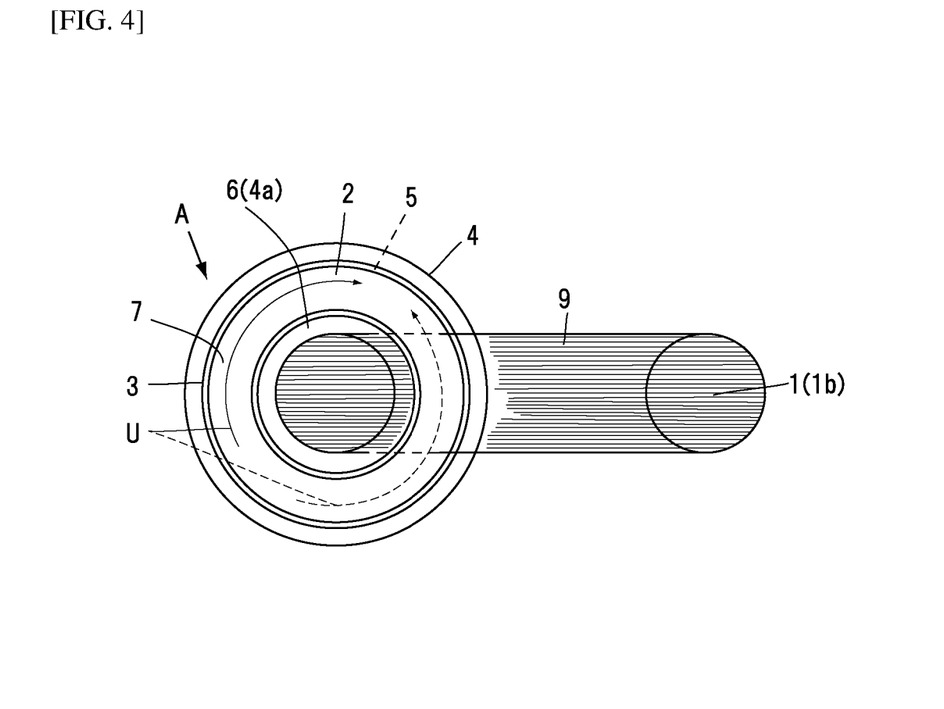
FIG. 4 is a plan view of FIG. 1.

As described above, the magnetic core 1 shown in FIG. 1 has a circular cross section and is suitable for the type of the liquid culture medium vessel 3 shown in FIG. 4. The magnetic core 1 shown in FIG. 10 is a magnetic core having a rectangular cross section and is suitable for the type of the liquid culture medium vessel 3 shown in FIG. 11.

The magnetic core 1 with low eddy current loss can anyway be obtained by laminating thin insulated sheets made of a magnetic material in a direction perpendicular to the magnetic flux in the core. Silicon steel sheets are suitable for use as the material of the magnetic core 1 due to its high saturation magnetization. It is desirable to use the magnetic core 1 having a shape that forms a closed magnetic path with a closed loop as shown in FIG. 1 and FIG. 10, if possible, because the magnetic core 1 with a closed loop has a smaller demagnetizing field and thus requires a lower excitation current to generate a required magnetic flux in the magnetic core 1. However, electrical stimulation effective for cells can be obtained without having to form a closed magnetic path as long as a sufficiently large current is applied thereto. Even in an open magnetic path, the demagnetizing field can be reduced by making the length of the magnetic path much larger than the cross-sectional area thereof (for example, by using a long rod-shaped core).

It is desirable that the magnetic core 1 includes a stage 4 on which the liquid culture medium vessel 3 is to be placed. Like the liquid culture medium vessel 3, the stage 4 also must be made of a non-magnetic and non-electrically conductive material. The stage 4 includes a through hole 4a formed at a position corresponding to that of the through hole 6.

In the case of the magnetic core 1 having a closed magnetic path, it must have a structure that can be divided into two parts, as described above (FIG. 1 and FIG. 10), so that the liquid culture medium vessel 3 can be mounted on the stage 4.

The magnetic core 1 is mounted in the following manner. As shown in FIG. 2, one end of the upper core 1a as one part of the magnetic core 1 is pivotally moved and separated from the lower core 1b as the other part of the magnetic core 1, a portion of the lower core 1b that projects through the stage 4 thereof is inserted through the through hole 6 of the liquid culture medium vessel 3, and then the one end of the upper core 1a is moved back and connected to the lower core 1b. Thus, electrical stimulation can be applied. In this case, unlike conventional immersed electrodes, the magnetic core 1 is not in contact with the liquid culture medium 2. Therefore, electrical stimulation can be applied merely by replacing the liquid culture medium vessel 3 with a new one, without the need for sterilization of such conventional immersed electrodes. This is one of the major advantages of the apparatus of the present invention.

The excitation coil 5 is typically formed by winding a copper wire several to several tens of times. As the number of turns of the coil increases, the inductance increases and thus the output voltage required for the coil power supply 8 increases. On the other hand, when the number of turns is small, a high output current is required for the coil power supply 8. It is preferable to use, as the coil power supply 8, a high capacity, high speed bipolar power supply or a pulsed power supply dedicated to pulse generation. It is also possible to use an alternating current power supply as the coil power supply 8.

When strong electrical stimulation has to be applied, it is preferable to wind the excitation coil 5 around the magnetic core 1 at a position near the liquid culture medium vessel 3.

Even if the magnetic core 1 has a closed magnetic path, a small portion of the magnetic flux leaks from the surface thereof. Therefore, when the excitation coil 5 is disposed at a distance from the liquid culture medium vessel 3, a portion of the magnetic flux generated near the excitation coil 5 leaks out of the magnet core 1 before passing through the liquid culture medium vessel 3, and as a result, the magnitude of the magnetic flux passing through the liquid culture medium vessel 3 is reduced.

FIG. 7 to FIG. 9 show modified examples of the liquid culture medium vessel 3. These modified liquid culture medium vessels 3 each include a reduced path 7a in the ring-shaped recess 7 to reduce the cross-sectional area of a portion of the current-carrying path for the eddy current U, as described above.

FIG. 8 shows a type of the liquid culture medium vessel, in which a portion of the ring-shaped recess 7 (a portion corresponding to the reduced path 7a) has a depth shallower than the depth of the other portion of the ring-shaped recess 7 and thus has a current-carrying cross-sectional area S1 that is smaller than the current-carrying cross-sectional area S2 of the other portion. FIG. 9 shows another type of the liquid culture medium vessel, in which a portion of the ring-shaped recess 7 (a portion corresponding to the reduced path 7a) has a width narrower than the width of the other portion of the ring-shaped recess 7 and thus has a smaller current-carrying cross-sectional area S1.

Both the depth and the width of a portion of the ring-shaped recess may be reduced as well. By reducing the cross-sectional area of a portion of the current-carrying path (a portion corresponding to the reduced path 7a), the density of the eddy current flowing in that portion can be increased and further the intensity of the electric field therein can also be increased. As a result, a high current density (and a high electric field) can be obtained in a portion of the liquid culture medium 2 (a portion corresponding to the reduced path 7a), and strong stimulation can be applied selectively to only a fraction of the cells in the liquid culture medium. In addition, when a sufficiently high current density cannot be obtained by using an ordinary liquid culture medium vessel due to electrical and dimensional constraints, this technique can be used to increase the current density and thus to achieve a target current density level.

EXAMPLES

Next, the present invention will be described in detail with reference to a specific example. This example is given for easy understanding by those skilled in the art. Therefore, it should be understood that the present invention is limited only by the technical ideas described throughout the description and should not be limited only by this example.

Example 1

A silicon steel strip having a width of 90 mm and a thickness of 0.27 mm was wound about 230 times around a mandrel of 100 mm×80 mm to obtain a wound core having a magnetic path with a cross-sectional area of 90 mm×65 mm and a length of 560 mm. This wound core was divided into two parts and thus a magnetic core was obtained. A liquid culture medium vessel made of glass and having a ring-shaped recess with a width of 16 mm, a depth of 18 mm, and a ring length of 400 mm was prepared. The glass had a thickness of 2 mm, and the vessel had a width of 108 mm, a length of 134 mm, and a height of 20 mm. A through hole of 68 mm×94 mm was formed at the center of the vessel within the ring-shaped recess. A flat rectangular wire of 1 mm×11 mm was wound four times around the magnetic core so that the wound wire served as an excitation coil. A pulsed power supply was used as a coil power supply and connected to the excitation coil with cables of 8 mm square. A plate made of glass-epoxy serving as a stage was attached to the magnetic core. The liquid culture medium vessel was placed on the stage in such a manner that a portion of the magnetic core thus obtained was inserted through the through hole. Then, a 0.9% saline solution was poured into the liquid culture medium vessel to a depth of 15 mm. As a result, a structure as shown in FIG. 1 was prepared.

When the structure as shown in FIG. 1 was prepared, the coil power supply was caused to generate a pulse voltage of 600 V. As a result, the excitation coil was energized with a pulse current of about 1100 A. The pulse width of the pulse current was about 100 µs. A partition wall was placed at a position in the ring-shaped recess of the liquid culture medium vessel to prevent the flow of an eddy current, and then the potential difference between the two sides of the wall was measured. As a result, it was found that a potential difference of 115 V occurred simultaneously with the generation of the pulse current in the excitation coil. This result seems to indicate that this structure can generate an electric field of about 115 V/400 mm=287.5 V/m.

Next, the partition wall was removed and a three-dimensional cultured muscle having a length of about 10 mm was placed in the liquid culture medium. This three-dimensional cultured muscle is a group of muscle cells and is known to contract when a voltage of 40 V with a pulse width of 1 ms was applied thereto using electrodes placed at a distance of 50 mm. When, in this state, a pulse voltage of 600 V was generated in the same manner as described above, the excitation coil was energized with a pulse current of about 1100 A. The pulse width of the pulse current was about 100 is. Under these conditions, no contraction of the three-dimensional cultured muscle was observed.

Next, several glass-epoxy plates of 15 mm×15 mm with a thickness of 0.5 mm were stacked on the bottom of the liquid culture medium vessel so as to reduce the cross-sectional area of a portion of the current-carrying path (with a length of 15 mm) in the liquid culture medium to one sixth. When, in this state, a pulse voltage of 600 V was generated in the same manner as described above, the excitation coil was energized with a pulse current of about 1100 A. The pulse width of the pulse current was about 100 µs. Under these conditions, it was observed that when the three-dimensional cultured muscle was electrically stimulated, it contracted in synchronization with the generation of the pulse voltage. This fact reveals that a current density high enough to induce contraction of the three-dimensional cultured muscle could be generated around the three-dimensional cultured muscle without using electrodes.

INDUSTRIAL APPLICABILITY

The devices of the present invention can be very important to the study of the control of various types of cells including pluripotent stem cells such as iPS cells and ES cells and to the manufacture of products using such cells.

REFERENCE SIGNS LIST

A: Electrical stimulation apparatus
S1, S2: Current-carrying cross-sectional area
U: Eddy current
g: Magnetic flux direction
1: Magnetic core
1a: Upper core
1b: Lower core
2: Liquid culture medium
3: Liquid culture medium vessel
4: Stage
4a: Through hole
5: Excitation coil
6: Through hole
7: Ring-shaped recess
7a: Reduced path
8: Coil power supply
9: Electromagnetic steel sheet

The invention claimed is:
1. An apparatus for non-contact electrical stimulation of cells in a liquid culture medium, comprising:
   a liquid culture medium vessel including: a ring-shaped recess for holding a liquid culture medium; and a through hole formed within the ring-shaped recess;
   a magnetic core made of a ferromagnetic material and disposed such that a portion of the magnetic core is inserted through the through hole of the liquid culture medium vessel;
   an excitation coil wound around the magnetic core; and
   a coil power supply for supplying a varying current to the excitation coil.

2. The apparatus for non-contact electrical stimulation of cells in a liquid culture medium according to claim 1, wherein the magnetic core forms a closed magnetic path.

3. The apparatus for non-contact electrical stimulation of cells in a liquid culture medium according to claim 1, wherein the ring-shaped recess of the liquid culture medium vessel includes a reduced path serving as a current-carrying path for an eddy current induced in the liquid culture medium, and the reduced path has a current-carrying cross-sectional area that is smaller than a current-carrying cross-sectional area of a portion other than the reduced path of the ring-shaped recess.

4. The apparatus for non-contact electrical stimulation of cells in a liquid culture medium according to claim 1, wherein the magnetic core is composed of electromagnetic steel sheets laminated in a direction perpendicular to a direction of a magnetic flux generated in the magnetic core.

5. A method for electrical stimulation of target cells in a liquid culture medium using the apparatus for non-contact electrical stimulation according to claim 1, comprising:

introducing a liquid culture medium containing target cells into the ring-shaped recess formed in the liquid culture medium vessel;

disposing the magnetic core made of a ferromagnetic material such that a portion of the magnetic core is inserted through the through hole formed within the ring-shaped recess of the liquid culture medium vessel; and energizing the excitation coil wound around the magnetic core to generate a magnetic flux in the magnetic core, so that the magnetic flux induces a varying eddy current and a varying electric field in the liquid culture medium held in the liquid culture medium vessel and thereby the target cells contained in the liquid culture medium in the ring-shaped recess are electrically stimulated by the induced eddy current and electric field.

* * * * *